US011181529B2

(12) United States Patent
Weinberger et al.

(10) Patent No.: US 11,181,529 B2
(45) Date of Patent: Nov. 23, 2021

(54) RADICAL DOSIMETRY FOR ANALYSIS OF BIOPHARMACEUTICALS AND BIOLOGICAL MOLECULES

(71) Applicant: GenNext Technologies, Inc., Montara, CA (US)

(72) Inventors: Scot Randy Weinberger, Montara, CA (US); Joshua S. Sharp, Oxford, MS (US); Sandeep Misra, Oxford, MS (US)

(73) Assignee: GenNext Technologies, Inc., Half Moon Bay, CA (US)

( * ) Notice: Subject to any disclaimer, the term of this patent is extended or adjusted under 35 U.S.C. 154(b) by 0 days.

(21) Appl. No.: 17/193,913

(22) Filed: Mar. 5, 2021

(65) Prior Publication Data

US 2021/0223255 A1 Jul. 22, 2021

Related U.S. Application Data

(63) Continuation-in-part of application No. PCT/US2020/012430, filed on Jan. 6, 2020, and a continuation-in-part of application No. PCT/US2019/057059, filed on Oct. 18, 2019, said application No. PCT/US2020/012430 is a continuation-in-part of application No. 16/316,006, filed on Jan. 7, 2019, now Pat. No. 10,816,468, said
(Continued)

(51) Int. Cl.
*G01N 33/68* (2006.01)
*G01N 21/64* (2006.01)
*G01N 21/33* (2006.01)

(52) U.S. Cl.
CPC ......... *G01N 33/6803* (2013.01); *G01N 21/33* (2013.01); *G01N 21/6428* (2013.01); *Y10T 436/203332* (2015.01)

(58) Field of Classification Search
CPC ............... G01N 33/68; G01N 33/6803; G01N 33/6848; G01N 21/6428; G01N 21/33; Y10T 436/203332; Y10T 436/2575
USPC ................... 436/86, 89, 164, 172, 180, 131; 422/82.05, 82.08, 82.09, 502, 503
See application file for complete search history.

(56) References Cited

U.S. PATENT DOCUMENTS 9,279,814 B2 * 3/2016 Brenowitz ............ B01L 3/5027
10,816,468 B2 * 10/2020 Weinberger .......... G01N 21/631
(Continued)

FOREIGN PATENT DOCUMENTS

WO 2018/218163 A1 11/2018

OTHER PUBLICATIONS

Roush et al. bioRxiv, pp. 1-6, Oct. 19, 2019.*
(Continued)

*Primary Examiner* — Maureen Wallenhorst
(74) *Attorney, Agent, or Firm* — Rimon Law, P.C.

(57) ABSTRACT

The three-dimensional structural analysis of pharmaceutical and/or biological molecules is performed by the reaction of OH radicals on the surfaces of the molecules of interest. Quantitation and/or completeness of the OH radicals are optionally measured using buffers intrinsic to the sample solutions as internal standards. Measurements of the reactions of these buffers with OH radicals provide an internal standard while avoiding the use of prior art internal standards that can have unwanted effects on the three-dimensional structures of interest.

24 Claims, 7 Drawing Sheets

Related U.S. Application Data application No. PCT/US2019/057059 is a continuation-in-part of application No. 16/316,006, filed on Jan. 7, 2019, now Pat. No. 10,816,468, said application No. PCT/US2020/012430.

(60) Provisional application No. 62/747,247, filed on Oct. 18, 2018, provisional application No. 62/788,219, filed on Jan. 4, 2019.

(56) References Cited

U.S. PATENT DOCUMENTS

| | | |
|---|---|---|
| 2003/0074062 A1 | 4/2003 | Monzyk et al. |
| 2006/0257877 A1 | 11/2006 | Anderle et al. |
| 2008/0165363 A1 | 7/2008 | Gusev |
| 2014/0030751 A1 | 1/2014 | Sharp |

OTHER PUBLICATIONS

Sharp et al. Analytical Chemistry, vol. 90, p. 12625-12630, Oct. 5, 2018.*
Xie et al. Analytical Chemistry, vol. 87, p. 10719-10723, Oct. 11, 2015.*
PCT/US2019/057059, International Search Report and Written Opinion, dated Dec. 31, 2019.

* cited by examiner

RADICAL DOSIMETRY FOR ANALYSIS OF BIOPHARMACEUTICALS AND BIOLOGICAL MOLECULES

CROSS REFERENCE TO RELATED APPLICATIONS

This application is a continuation-in-part of PCT/US20/12430 filed on Jan. 6, 2020 and also a continuation-in-part of PCT/US19/57059, filed Oct. 18, 2019, both PCT/US20/12430 and PCT/US19/57059 are continuations-in-part of U.S. non-provisional patent application Ser. No. 16/316,006 filed Jan. 7, 2019, now U.S. Pat. No. 10,816,468; U.S. non-provisional application Ser. No. 16/316,006 claims priority to U.S. provisional patent applications Ser. No. 62/747,247 filed Oct. 18, 2018 and 62/788,219 filed Jan. 4, 2019; PCT/US19/57059 further directly claims priority to U.S. provisional patent application Ser. No. 62/747,247 filed Oct. 18, 2018; PCT/US20/12430 and PCT/US19/57059 both also claim priority and benefit of U.S. provisional patent application Ser. No. 62/788,219 filed Jan. 4, 2019. All of the above patent applications are hereby incorporated herein by reference.

STATEMENT OF GOVERNMENT SUPPORT

This invention was made with government support under grants R01GM127267 and R43GM125420 awarded by the National Institute of General Medical Sciences. The Government has certain rights in the invention.

BACKGROUND

Field of the Invention

The present invention relates to a device and methodologies for higher order structural analysis of biomolecules by the process of hydroxyl radical protein-footprinting. More specifically, some embodiments of the present invention relate to the determination of biopharmaceutical tertiary and quaternary structure and associated conformation using improved devices and methodologies for flash photo-oxidation of proteins to determine their higher order biomolecular structure.

Related Art

The discussion of any work, publications, sales, or activity anywhere in this submission, including in any documents submitted with this application, shall not be taken as an admission that any such work constitutes prior art. The discussion of any activity, work, or publication herein is not an admission that such activity, work, or publication existed or was known in any particular jurisdiction.

During the last thirty years, the popularity and use of biopharmaceuticals has prospered, fostering substantial growth in the biopharmaceutical industry (*Global biopharmaceuticals market growth, trends and forecasts* (2016-2021), in Current trends in biopharmaceuticals market; 2016). This growth was fueled by the introduction of key recombinant drugs with efficacy in combating metabolic, rheumatoid-arthritic, auto-immune, and neoplastic disease (*Shaping the biosimilars opportunity: a global perspective on the evolving biosimilars landscape*; IMS Health, 2011). While effective, bio-therapeutics are expensive and exert substantial financial pressure upon patients and healthcare delivery (*MedPAC. Medicare payment systems and follow-on biologics, Report to Congress: Improving Incentives in the Medicare Program;* 2009). Recently, the biopharmaceutical market has been impacted by two key events: a worldwide financial crisis that has forced healthcare systems to achieve significant cost reduction; and an unprecedented level of patent expirations for many of the world's largest brands, setting the stage for biosimilar development (Schellekens, H., *Biosimilar therapeutics—what do we need to consider?*, Nephrol Dial Transplant; 2009). Biosimilars are therapeutics similar to but not identical to existing innovator or reference products. Unlike the case for small molecule drugs, biosimilars are not merely generic versions of original products. Conventional generics are considered to be therapeutically and molecularly equivalent to their originators. This is simply not the case with biosimilars, which are complex, three-dimensional biomolecules, whose heterogeneity and dependence upon production in living cells makes them quite different from classical drugs. The structures and functional activities of bio-therapeutics are exquisitely sensitive to their environments. The intended structure of a therapeutic is maintained by a delicate balance of factors, including concentration of the protein, control of post-translational modifications, pH as well as co-solutes in the formulation, and production/purification schemes (Gabrielson, J. P.; Weiss I V, W. F., *Technical decision-making with higher order structure data: starting a new dialogue*; Journal of pharmaceutical sciences, 2015). As such, the biopharmaceutical structure of biosimilars is preferably prudently maintained, for if not held in check, undesirable and adverse pharmacological consequences can arise.

Adverse drug reactions (ADR) of biopharmaceuticals are typically attributed to exaggerated pharmacology as well as immunological reactions. The range of patient ADR's extends from symptomatic irritation to morbidity and death. While the etiology for some ADR's may be traced to patient pharmacogenomics sensitivity, many are attributed to intrinsic properties of the therapeutic, which has resulted in morbid and fatal patient consequences and substantial financial loss to the biotherapeutic industry (Giezen, T. J.; Schneider, C. K., *Safety assessment of biosimilars in Europe: a regulatory perspective*; Generics and Biosimilars Initiative Journal; 2014). As such, the occurrence of catastrophic ADR's has exemplified the need for improved analytics for the development and quality control of biopharmaceuticals.

In order to minimize ADR's and to facilitate the development of biosimilars, the FDA, the Center for Drug Evaluation and Research, and the Center for Biologics Evaluation and Research have issued guidelines that stress the use of state-of-the art technology for evaluating protein higher order structure (HOS) (*Quality considerations in demonstrating bio-similarity of a therapeutic protein product to a reference product; guidance for industry*; U.S. Department of Health and Human Services; Food and Drug Administration; Center for Drug Evaluation and Research; Center for Biologics Evaluation and Research Washington, D.C.; 2015). HOS analysis involves the determination of the tertiary and quaternary structure and associated conformation of a given biomolecule. Such biomolecules include protein and protein conjugates which may or may not be considered to be a biotherapeutic agent. Although a variety of HOS analytics exist today, their inadequacies to reliably predict biotherapeutic efficacy and safety has been brought into question, establishing the unmet need for new and improved HOS analytics (Gabrielson, J. P.; Weiss I V, W. F., *Technical decision-making with higher order structure data: starting a new dialogue*; Journal of pharmaceutical sciences; 2015).

A promising and emerging technique to address the unmet need for HOS analysis is irreversible protein hydroxylation, in combination with mass spectrometry (MS), (Hambly, D. M.; Gross, M. L., *Laser flash photolysis of hydrogen peroxide to oxidize protein solvent-accessible residues on the microsecond timescale*; Journal of the American Society for Mass Spectrometry; 2005). This process has been coined hydroxyl radical protein foot-printing (HRPF). A variety of techniques have been used to perform HRPF. Perhaps the most widely used approach relies upon fast photochemical oxidation of proteins (FPOP) that generates hydroxyl (OH) radicals from hydrogen peroxide ($H_2O_2$) using a single, high fluence, short pulse of UV light. The reaction of OH radicals and solvent exposed amino acids typically results in net insertion of one oxygen atom into the amino acid. OH radicals are short-lived, and when generated by a brief UV pulse, reactions between amino acids and radicals are completed before any conformation change by the labeled protein can occur (Konermann, L.; Tong, X.; Pan, Y., *Protein structure and dynamics studied by mass spectrometry: H/D exchange, hydroxyl radical labeling, and related approaches*; Journal of mass spectrometry; 2008). The mass spectra of the peptide products of enzyme digestion show various levels of oxidation marked by peak shifts of 16 Da, 32 Da, 48 Da, etc.

While the analytical attributes of FPOP are impressive, its impact upon HOS analysis has been constrained by limited adoption within the biopharmaceutical research community. A technical limitation of FPOP HRPF that deleteriously impacts comparative studies stems from the reaction of OH radicals with non-analyte components in the sample, such as buffer constituents and incipient solutes. Variability in the rate of background scavenging causes trial-to-trial irreproducibility, which has limited comparative studies (Niu, B. et al.; *Dosimetry determines the initial OH radical concentration in fast photochemical oxidation of proteins (FPOP)*; Journal of the American Society for Mass Spectrometry; 2015). While OH radicals are excellent probes of protein topography, they also react with many compounds found in analytical preparations. Competition between analyte protein and background scavengers for free OH radicals exists, making it necessary to measure the effective concentration of radical available to oxidize a target protein to insure reproducible results.

Prior art teaches radical dosimetry as performed using spiked peptide internal standards (Niu, B., et al., *Dosimetry determines the initial OH radical concentration in fast photochemical oxidation of proteins (FPOP)*. J Am Soc Mass Spectrom, 2015. 26(5): p. 843-6; Niu, B., et al., *Incorporation of a Reporter Peptide in FPOP Compensates for Adventitious Scavengers and Permits Time-Dependent Measurements*. J Am Soc Mass Spectrom, 2016.), or a UV absorbing internal standard, such as adenine, added to the buffer and assessed in a post-labeling manner (Xie, B.; Sharp, J. S., Hydroxyl Radical Dosimetry for High Flux Hydroxyl Radical Protein Footprinting Applications Using a Simple Optical Detection Method. *Analytical chemistry* 2015, 87 (21), 10719-23.). In peptide radical dosimetry, labeled peptide and target protein are subsequently analyzed using LC-MS (with optional proteolysis) to assess the relative ratio of oxidized peptide to that of the target protein. Should the desired peptide to protein oxidation ratio not be achieved, the entire experiment is repeated adjusting the concentration of $H_2O_2$ dependent upon the need to either increase or decrease effective OH radical load. For adenine dosimetry, the effective change in adenine UV absorbance is determined upon completion of the labeling process, and the ratio of the achieved vs target adenine UV absorbance change is determined. The $H_2O_2$ concentration is subsequently varied in accordance with the desired change in UV absorbance. Both of these approaches are performed after labeling has been completed and do not enable real-time adjustment of effective OH radical load, consuming precious sample and needlessly wasting investigator time. This is a significant disadvantage.

SUMMARY OF THE INVENTION

The present invention is directed to systems and methods for the analysis of protein higher order structure comprising improved embodiments to perform flash photo-oxidation of proteins enabling advanced hydroxyl radical protein foot-printing. In some embodiments, the invention provides an in-line radical dosimetry system wherein closed-loop control is established between the flash photolysis system and dosimeter to control irradiance of the flash photolysis system in response to measured changes in absorbance of an internal standard radical dosimeter, for which the internal standard radical dosimeter is the buffer component of a biological preparation.

In photochemistry, effective radical concentration is measured using a radical dosimeter internal standard. Ideally, a dosimeter would have: a simple relationship between effective radical concentration and dosimeter response; a simple, rapid, and non-destructive measurement means; and be unreactive to most proteins. As such, an improved embodiment for FPOP HRPF analysis would include means and methodology to perform radical dosimetry, in real-time, to assess and correct for trial-to-trial variation of background scavenging during the sample photo-oxidation process.

In some embodiments, the invention provides an in-line radical dosimetry system wherein closed-loop control is established between an automated, in-line micro-fluidic mixing system and dosimeter to control the concentration of $H_2O_2$ in response to measured changes in absorbance of an internal standard radical dosimeter, for which the internal standard radical dosimeter is a buffer component or the primary buffer component of a biological preparation. The buffer may be selected to act as an internal standard to measure OH radical reactions and to cause minimal changes to the three-dimensional structure of the molecular analyte. For example, the buffer may be selected to maintain a physiological pH such that the molecular analyte has a three-dimensional structure similar to that found in situ.

In some embodiments, the invention provides an in-line radical dosimetry system wherein closed-loop control is established between the flash photolysis system and dosimeter to control irradiance of the flash photolysis system in response to measured changes in absorbance of an internal standard radical dosimeter, for which the internal standard radical dosimeter is a buffer component of a biological preparation, and OH radicals are created by the photolysis of $H_2O_2$.

In some embodiments, the invention provides an in-line radical dosimetry system wherein closed-loop control is established between the flash photolysis system and dosimeter to control irradiance of the flash photolysis system in response to measured changes in absorbance of an internal standard radical dosimeter, for which the internal standard radical dosimeter is a buffer component of a biological preparation, and OH radicals are created from water using photo-catalytic metal oxides.

In some embodiments, using an in-line radical dosimetry system, the invention provides a method of producing labeled protein for analysis comprising: (1) mixing protein sample with a biological buffer and other required labeling reagents, (2) introducing said sample into a photolysis cell, (3) determining the nascent photometric properties of said sample, (4) photo-irradiating said sample with at least one burst of UV irradiation, (5) determining the change in photometric properties for said sample after photo-irradiation, and (6) adjusting the spectral irradiance of the UV source light in accordance with the change in radical dosimeter photometric property.

In some embodiments, using an in-line radical dosimetry system, the invention provides a method of producing labeled protein for analysis comprising: (1) mixing protein sample with a biological buffer and other required labeling reagents, (2) introducing said sample into a photolysis cell, (3) determining the nascent photometric properties of said sample, (4) photo-irradiating said sample with at least one burst of UV irradiation, (5) determining the change in photometric properties for said sample after photo-irradiation, and (6) adjusting the concentration of $H_2O_2$ using an in-line, microfluidic mixer in accordance with the change in radical dosimeter photometric property.

In some embodiments, using an in-line radical dosimetry system, the invention provides a method of producing labeled protein for analysis comprising: (1) mixing protein sample with a biological buffer and metal-oxide photocatalyst, (2) introducing said sample into a photolysis cell, where the sample (3) determining the nascent photometric properties of said sample, (4) photo-irradiating said sample with at least one burst of UV irradiation, (5) determining the change in photometric properties for said sample after photo-irradiation, and (6) adjusting the spectral irradiance of the UV source light in accordance with the change in radical dosimeter photometric property.

Various embodiments of the invention include analysis system comprising: a flash photolysis system for irradiating a sample containing a photo-reactive sample mixture, the sample mixture including at least a molecular analyte and a buffer, the flash photolysis system being configured to cause OH radical reactions with both the analyte and the buffer; a photolysis cell in optical communication with the flash photolysis system light source and configured to receive the sample containing the photo-reactive sample mixture; a radical dosimeter configured for detecting photometric properties of the buffer; and feed-back logic configured to further irradiate the sample using the flash photolysis system responsive to the measured photometric properties of the buffer, the buffer selected to function as an internal standard indicative of a quantitation of OH radical reactions with the molecular analyte.

Various embodiments of the invention include a method of determining a three-dimensional structure of a molecular analyte, the method comprising: introducing a sample mixture into the photolysis cell of a flash photolysis system, the sample mixture including at least a molecular analyte and a buffer; determining a photometric property of the mixture; irradiating the sample mixture with at least a first light pulse from a pump light source, the first light pulse being configured to cause OH radical reactions with both the molecular analyte and the buffer; determining the change in photometric property of the sample mixture, the change including a change in photometric property of the buffer and representing a measure of OH radical reactions with the molecular analyte; irradiating the mixture with at least a second light pulse from the pump light source in response to the change in photometric property of the buffer, the second light pulse being configured to cause additional OH radical reactions with both the molecular analyte and the buffer; and analyzing the product produced from the irradiated sample mixture to generate data regarding a three-dimensional structure of the molecular analyte.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized. Further, the above objects and advantages of the invention will become readily apparent to those skilled in the art from reading the following description of a preferred embodiment when considered in the light of the accompanying figures that incorporate features of the present invention. The components in the drawings are not necessarily to scale, emphasis instead being placed upon clearly illustrating the principles of the present disclosure.

Any of the methods described herein can according to specific embodiments further comprise any one or more of the following of which.

DETAILED DESCRIPTION

Figure 1:
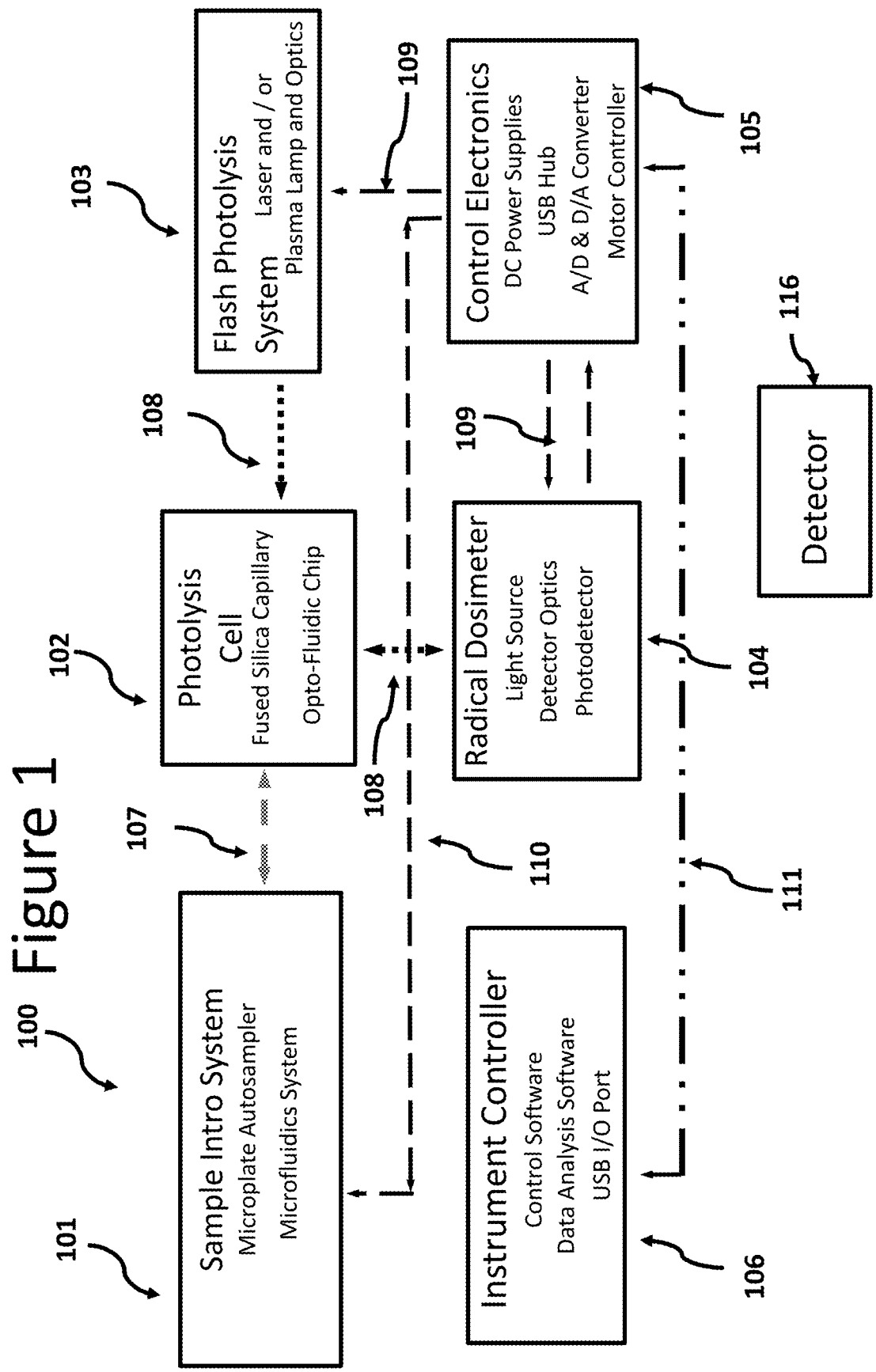
FIG. 1 illustrates a flash photo oxidation apparatus 100 with real-time radical dosimetry comprised of a number of subassemblies, according to various embodiments.

Systems and methods are provided for the analysis of molecular higher order structure. The analysis is accomplished by selective labeling solvent exposed molecular groups (e.g., those molecular groups that tend to be on the surface in the three dimensional structure of a biomolecule), as catalyzed by fast photo-oxidation with real-time monitoring and control of effective OH radical concentration. The systems and methods can be applicable to a variety of research fields, such as: general protein biochemistry; biopharmaceutical research and development; antibody research and development; therapeutic antibody research and development; and small molecule drug research and development. Moreover, the systems and methods can be applicable to a variety of research analyses such as: protein-ligand interaction analysis; protein-protein interaction analysis; protein-fusion product analysis; protein conformation and conformational change analysis; small drug molecule mode of action analysis; biopharmaceutical mode of action analysis; antibody-antigen analysis; protein epitope mapping; protein paratope mapping; and chemical reaction monitoring. Further, the systems and methods can comprise a biopharmaceutical production quality control analyzer for the following pharmaceutical products: monoclonal antibodies; polyclonal antibodies; antibody-drug conjugates; bioactive proteins; therapeutic enzymes; and other protein- or conjugated protein-based drugs.

In various embodiments, the systems described herein can receive analytical sample for subsequent chemical labeling via a step-wise introduction of previously analyzed or purified sample by manually pipetting the sample into appropriate micro-centrifuge tubes or microplates that are placed into the system's sample introduction assembly. Alternatively, the systems can be hyphenated with and receive sample directly from other separation and analysis instruments such as but not limited those which perform: liquid chromatography (LC), including reverse phase, normal phase, ion exchange, size exclusion, bio-recognition affinity, and hydrophilic interaction modes of separation; field-flow fractionation; capillary zone electrophoresis; and capillary isoelectric focusing electrophoresis. The before noted separation techniques may also be hyphenated with but not limited to the following detection schemes: ultraviolet, visible, and infra-red photometric absorbance; refractive index; light scattering; chemiluminescence; fluorescence; radiometric; voltametric; amperometric; and mass spectrometric detection. Detector 116 may be based on any of these analysis and/or separation techniques. For example detector 116 can include a mass spectrometer, MS/MS, and/or chromatography system. Detector 116 is optionally directly coupled to a microfluidics system that includes photolysis cell 102. Detector 116 is optionally configured to determine which amino acids or organic compounds of the analyte molecule which are hydroxylated by the OH radicals in the photolysis cell. Detector 116 is optionally configured to detect, small samples, for example, on the order of a few microliters, containing an analyte, e.g., a molecular analyte such as a biomolecule, pharmaceutical, and/or protein, to be measured by a systems or methods of the invention can be evaluated.

U.S. Provisional application 62/511,571 and International Application PCT/US18/34682 teach the means and methodology by which to perform radical dosimetry in real-time, as biologicals are labeled during the FPOP HRPF process. In this scheme, a photometric detection scheme is applied to the flowing stream of analyte in order to detect changes in the optical properties of an internal standard radical dosimeter. Optical property changes include but are not limited to: photometric absorbance, fluorescence; refractive index; and luminescence. Particular description is given to the use of adenine as an internal standard radical dosimeter that is added to the analytical sample as an exogenous or extrinsic component. Moreover, the '571 /'682 applications teach the means by which labeling parameters may be altered in real-time to achieve desired levels of effective OH radical concentration and associated labeling efficiency. Further, the '571/'682 application teaches the means by which effective OH radical yield can be controlled by varying the fluence and/or spectral irradiance of a plasma flash lamp source in addition to dithering $H_2O_2$ concentration. Additionally, the '571 /'682 applications teach the means by which FPOP HRPF can be performed using photo-catalytic metal oxides that function to generate OH radicals from water, thus eliminating the reliance upon $H_2O_2$.

The '571/682 applications teach a microfluidics system configured to move a sample mixture into a photolysis cell. The photolysis cell is in optical communication with the flash photolysis system light source and configured to receive the sample containing a photo-reactive sample mixture. Within this photolysis cell the mixture may be modified by OH radical reactions initiated by flash lamp and/or analyzed to measure the progress of the OH radical reactions. In some embodiments of the invention the photolysis cell is configured for the sample mixture to stay in the photolysis cell during both OH radical reactions and measurement of reaction progress. In other embodiments, reactions and measurement take place in different regions of the same microfluidics system and the microfluidics system is configured to move the sample mixture between these regions. In various embodiments, the movement between these regions may be of a travel distance less than 3, 5, 10, 15 20 or 30 mm, or any range there between.

While creating a real-time means to adjust and compensate for variation in background scavenging, the '571/'627 applications require the addition of an extrinsic internal standard dosimeter to the biological mixture. Under some conditions, the extrinsic internal standard may cause undesired artefactual changes in biomolecular higher order structure, and as such, be incompatible for the desired goal of providing a facile means of characterizing nascent higher order structure of biologicals. Embodiments of the present invention describe a device and methodologies by which commonly used biological buffer systems are employed as radical dosimeter internal standards. This greatly improves the utility of the technique and avoids the undesired changes in higher order structure that can be caused by internal standards of the prior art.

The photometric properties of some biological buffers are altered in a predictable manner upon OH radical attack. As such, these buffers can be employed as radical dosimeter internal standards, eliminating the need to add extrinsic reagents as standards. The buffers selected as internal standards include those whose solvating properties are known to stabilize or maintain nascent configurations of biomolecules. They are, therefore, unlikely to alter biological higher order structure in an undesirable manner Various embodiments of the invention include systems and methodologies that address shortcomings of prior art FPOP HRPF analysis by providing the means for real-time measurement and adjustment for unwanted background scavenging using the intrinsic properties of biological buffers.

General Overview of Instrument Components

This section provides a general overview of a flash photolysis instrument with in-line radical dosimeter that uses intrinsic photometric properties of a biological preparation buffer to assess and ultimately control effective OH radical concentration. A detailed description of each sub assembly is provided in ensuing passages. Moreover, an operational cascade that describes the interplay of these subassemblies is provided to enable understanding of typical instrument operation.

In various embodiments a flash photo oxidation apparatus 100 with real-time radical dosimetry is comprised of a number of subassemblies as illustrated in FIG. 1. Shown are: sample introduction system 101; photolysis cell 102; flash photolysis system 103; radical dosimeter 104; control electronics 105; instrument controller 106; fluidic inter-connection line 107 between the sample introduction system 101 and photolysis cell 102; fluidic inter-connection line 108 between the photolysis cell 102 and radical dosimeter 104; electronic inter-connects 109 between the radical dosimeter 104 and control electronics 105; electronic inter-connects 110 between the sample introduction system 101 and control electronics 105; electronic inter-connects 111 between the control electronics 105 and instrument controller 106; and detector 116.

Samples of interest are introduced via the sample introduction system 101. Samples can be presented using small volume micro-centrifuge tubes or by using multi-well microtiter plates as readily available from Eppendorf (Hamburg, Germany) Microfluidic circuitry provides the means for sample aspiration, transportation, as well as the transportation and deposition of oxidized product. Examples of applicable microfluidic circuitry are provided in U.S. Provisional application 62/511,571 and International Application PCT/US18/34682. They samples introduced can include a mixture of one or more molecular analyte and one or more buffer. In some embodiments, the buffer is selected to both control pH of the sample mixture and to operate as an internal standard to quantitate OH radical reactions with the one or more molecular analyte.

Sample photo-oxidation occurs within the instrument's photolysis cell 102. In one embodiment, photolysis cell 102 is comprised of a fused silica capillary as available from Polymicro Technologies—Molex (Phoenix, Ariz., USA). Typical capillary internal diameter can range from 50 micrometers to 1 mm. Typical wall thickness can range from 50-100 micrometers. In another embodiment, it is desired to use capillaries constructed with substantially thicker walls such as those which have outside diameters as large as 1-5 mm and internal diameters as small as 0.1 mm. In yet another embodiment, opto-fluidic chips can be fabricated using a variety of techniques, such as lithography assisted wet chemical etching, dry reactive ion etching, and laser ablation micro-structuring that create microfluidic channels within a quartz substrate. Fluidic and optical channel internal diameter can range from but are not limited to 0.1 to 1.0 mm. In another embodiment, fluidic and optical channels can have different internal diameters to ideally match disparate requirements of fluid transfer and optical coupling. Moreover, the opto-fluidic chip can contain an optical waveguiding structure, such as an integral optical fiber, monolithic waveguide, liquid core waveguide, or evanescent guiding means using metal oxides, rare-earth metals, or grating structures. In another embodiment at least one sample contacting surface of the photolysis cell is coated with a photocatalytic metal oxide, such as $TiO_2$. For some photocatalytic metal-oxide formulations, photolysis can be initiated using long UV (wavelength≥300 nm) or visible light. For these embodiments, capillaries and opto-fluidic chips can be fabricated using various varieties of glass, such as BK-7 or Borofloat® 33 (Schott AG, Germany), in lieu of fused silica or quartz. In another embodiment, quartz or glass opto-fluidic cells comprise a resonance structure to support resonance and/or multi-pass incident photon collision with dissolved reactants, such as but not limited to $H_2O_2$, suspended metal-oxide nanoparticles, or immobilized metal oxide films upon at least one sample contacting surface.

The photolysis cell receives sample from the sample system via a microfluidic path. After processing, oxidized sample within the photolysis cell is transferred into the radical dosimeter system 104. The photolysis cell is in optical communication with the flash photolysis system 103. Note that in some embodiments, both the oxidation by OH radicals and the measurement by the radical dosimeter system 104 is performed without moving the oxidized sample from within the photolysis cell. In other embodiments, the oxidized sample is moved a short distance between oxidation and measurement.

The photolysis cell 102 physically resides within the device's flash photolysis system 103. The photolysis system 103 is comprised of: a plasma flash lamp, or other appropriate light source such as an excimer laser, a solid state laser, or laser diode; and associated light collection/transmission optics match the requirements of the light transmission means to the photolysis zone.

The radical dosimeter 104 receives fluid from the photolysis cell 102, or in an alternative embodiment, the radical dosimeter 104 is incorporated into the photolysis cell by employing a different (e.g., an orthogonal) optical path. In these embodiments, OH radical generation, OH radical reaction with a molecular analyte and changes in photometric properties of the sample mixture can all take place in the same location.

A variety of photometric detection schemes may be employed by the radical dosimeter 104 to monitor the associated photometric properties of the internal standard dosimeter. The radical dosimeter 104 is configured to detect photometric properties of the buffer, and optionally of other species in the sample mixture with which OH radical reactions have occurred. This detection may occur in photolysis cell 102 and/or within a microfluidics system that includes the photolysis cell 102. For example, the radical dosimeter 104 may be configured for detecting the photometric properties of the buffer at a location within a microfluidics system that includes the photolysis cell, the location being between 3-30 mm from the photolysis cell, the micro fluidics system being configured for moving the sample mixture back and forth between the photolysis cell and the location at which the photometric properties of the buffer are detected. The radical dosimeter 104 optionally includes a light source separate from a light source of the flash photolysis system 103. The microfluidics system including the photolysis cell may be configured to convey light from both these light sources to the sample mixture.

In various embodiments, the internal standard dosimeter can be an extraneous additive that is spiked into the biological sample. For example, one or more buffers may be added to the sample for to function as internal standards. In some embodiments, the intrinsic photometric properties of the biological buffer system may serve as an intrinsic dosimeter standard. Both added and intrinsic buffers are optionally used in combination as internal standards. The radical dosimeter 104 detects changes in photometric properties that represent quantitation of OH reactions with the molecular analyte and/or the internal standard buffer. Changes in photometric properties of either or both the molecular analyte and buffer may be detected by the radical dosimeter 104.

Photometric detection schemes include but are not limited to: fluorescence, photometric absorbance, refractive index detection, light scatter detection, and luminescence. In one embodiment, the photometric detection scheme comprises an ultra-violet (UV) light photometric absorbance detector. For photometric UV absorbance detection, selective, narrow-bandwidth (≤15 nm) UV light is generated by a UV light source and is directed to probe the sample residing in photolysis cell in the region illuminated by the flash source. In an alternative embodiment, the UV light source is directed to probe the sample down-stream from the photolysis cell. When used in combination with an optical notch filter that passes light of suitable wavelength, applicable UV light sources include broad spectrum sources such as Hg, Xe, or deuterium plasma lamps. Alternatively, narrow bandwidth, solid state light emitting diode (LED) sources can be employed. In some embodiments, a 265 nm UV LED source is used such as available from Q-Photonics (Ann Arbor, Mich., USA). Light from the UV light source can be transmitted into the photolysis cell using a plurality of approaches: collimated light transmitted through free air; transmission via coupling to an optical fiber of appropriate composition and numerical aperture; and transmission using a liquid core waveguide. After probing the same, transmitted light is directed to impinge upon a photodetector using the above noted transmission means. In some embodiments, the photodetector comprises a silicon photo-diode assembly with optical transmission and photon-to-electron conversion efficiency in the wavelength domain of interest, such as the S1336-8BQ silicon photodiode available form Hamamatsu (Hamamatsu City, Japan). Photodiode output current is processed by a current to voltage (I to V) convertor, to provide a voltage that is proportional to photodiode incident light intensity. Photodiode output voltage is transmitted to the control electronics assembly 105, where an analog to digital converter (ADC) creates a digital signal that is ultimately transmitted to the instrument controller 106 where UV absorbance calculations are performed. Instrument controller 106 can include a personal computer and/or other computing device.

The control electronics assembly 105 functions to: provide direct current (DC) drive voltage, derived from laboratory alternating current (AC) power sources, to all peripheral assemblies; provide analog and digital control signals to peripheral devices; receive analog or digital information from peripheral devices; provide ADC and digital to analog conversion (DAC) functions; and provide data to and receive commands from the instrument controller 106. In a preferred embodiment, the control electronics assembly comprises a motor controller that interfaces with motors located within the sample introduction-collection system 101. Moreover, the control electronics assembly 105 optionally contains a universal serial bus (USB) hub or other port for digital communication with the instrument controller 106.

The instrument controller 106 functions to provide process control for various instrument peripheral devices while receiving status and data information from these devices in digital format. In some embodiments, the instrument controller 106 is configured to execute a software control program with at least two main modules: a low level, multi-threaded module for instrument component control and a high level user interface (UI) module. In other embodiments, the control electronics assembly 105 comprises an embedded microprocessor that provides low level instrument component control while communicating with a high level UI control program of the instrument controller 106 via a USB interface.

Control electronics assembly 105 and/or instrument controller 106 are components of feed-back logic. Feed-back logic is configured to use measurements made by radical dosimeter 104 to determine if the molecular analyte has undergone sufficient reactions with OH radicals to provide useful information on the three-dimensional structure of the molecular analyte. If additional reactions (e.g., doses of OH radicals) are desirable, then the feed-back logic is configured to further irradiate the sample using the flash photolysis system responsive to the measured photometric properties of the sample mixture. These photometric properties of the sample mixture include, and are optionally dominated by photometric properties of the buffer. In some embodiments, the buffer is selected to function as an internal standard indicative of a quantitation of OH radical reactions with the molecular analyte, optionally as well as to control the pH of the sample mixture to within a physiologically desirable or relevant pH range. In some embodiments, feed-back logic is configured to continue adjust characteristics (e.g., fluence, pulse number, wavelength, and/or irradiance, etc.) of the flash photolysis system so as to achieve a desired level of OH radical reactions. For example, flashes photolysis light may be applied until a predetermined threshold of change in the photometric properties of the buffer is reached. Optionally this threshold represents a reaction amount that is saturated or near saturation of oxidation of surface amino acids of the molecular sample.

Figure 3:
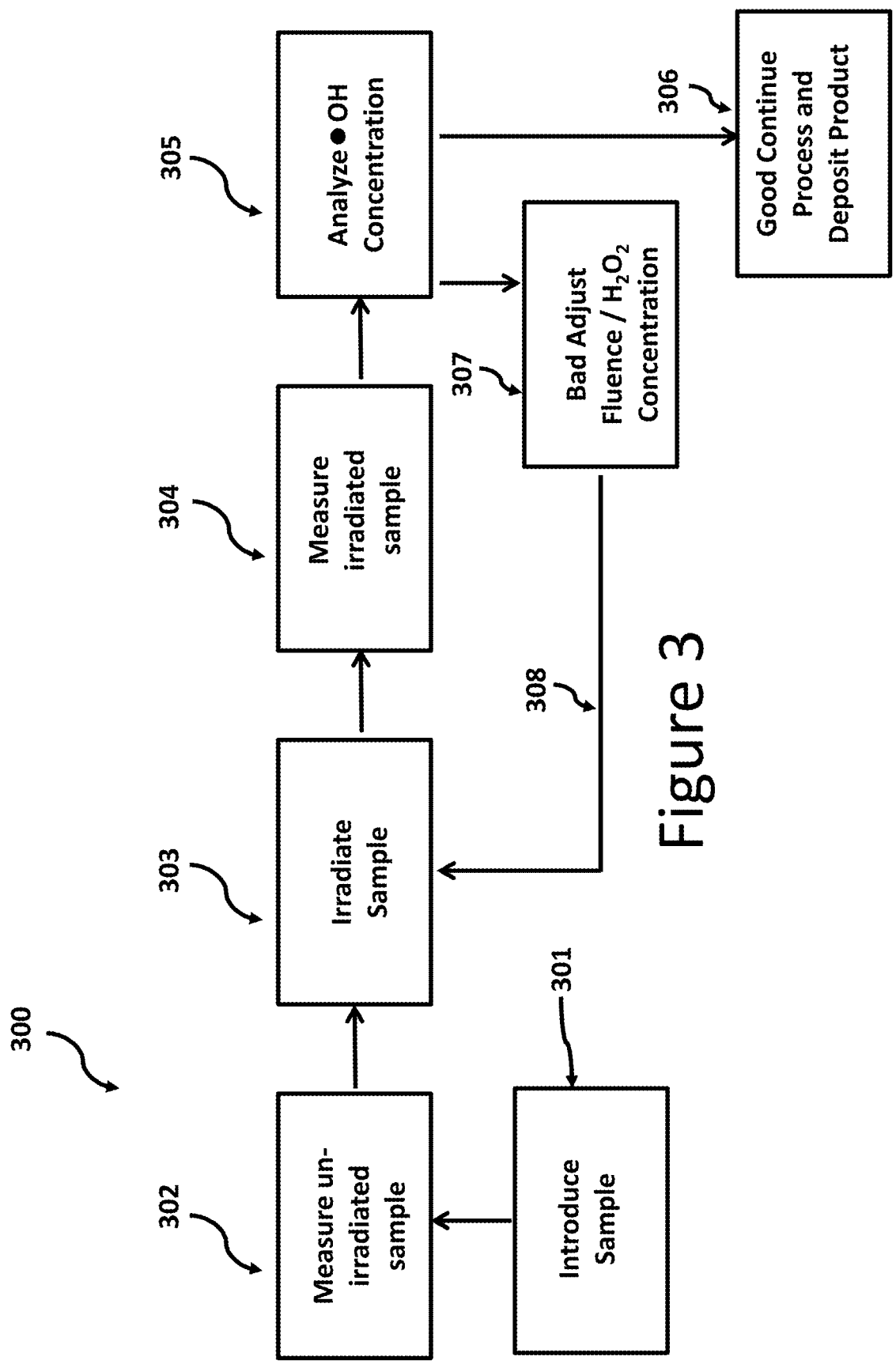
FIG. 3 illustrates methods of sample labeling and analysis, according to various embodiments of the invention.

In some embodiments, the feed-back logic of control electronics assembly 105 and/or instrument controller 106 is configured to irradiate the sample using the flash photolysis system and measure the photometric properties of the buffer within the photolysis cell, for several irradiation-measurement cycles (e.g., cycles represented by steps 303, 304, 306 and 307 discussed elsewhere herein with respect to FIG. 3) during which the sample remains in the photolysis cell or remains in a microfluidic system including the photolysis cell. In some embodiments, the feed-back logic is configured to repeat the irradiation-measurement cycles until a desired amount of reaction, as indicated by change in photometric properties, between the buffer and OH radicals has been achieved.

Detailed Overview of Instrument Components and Operation

Sample Introduction, Sample Processing and Product Collection

Figure 2:
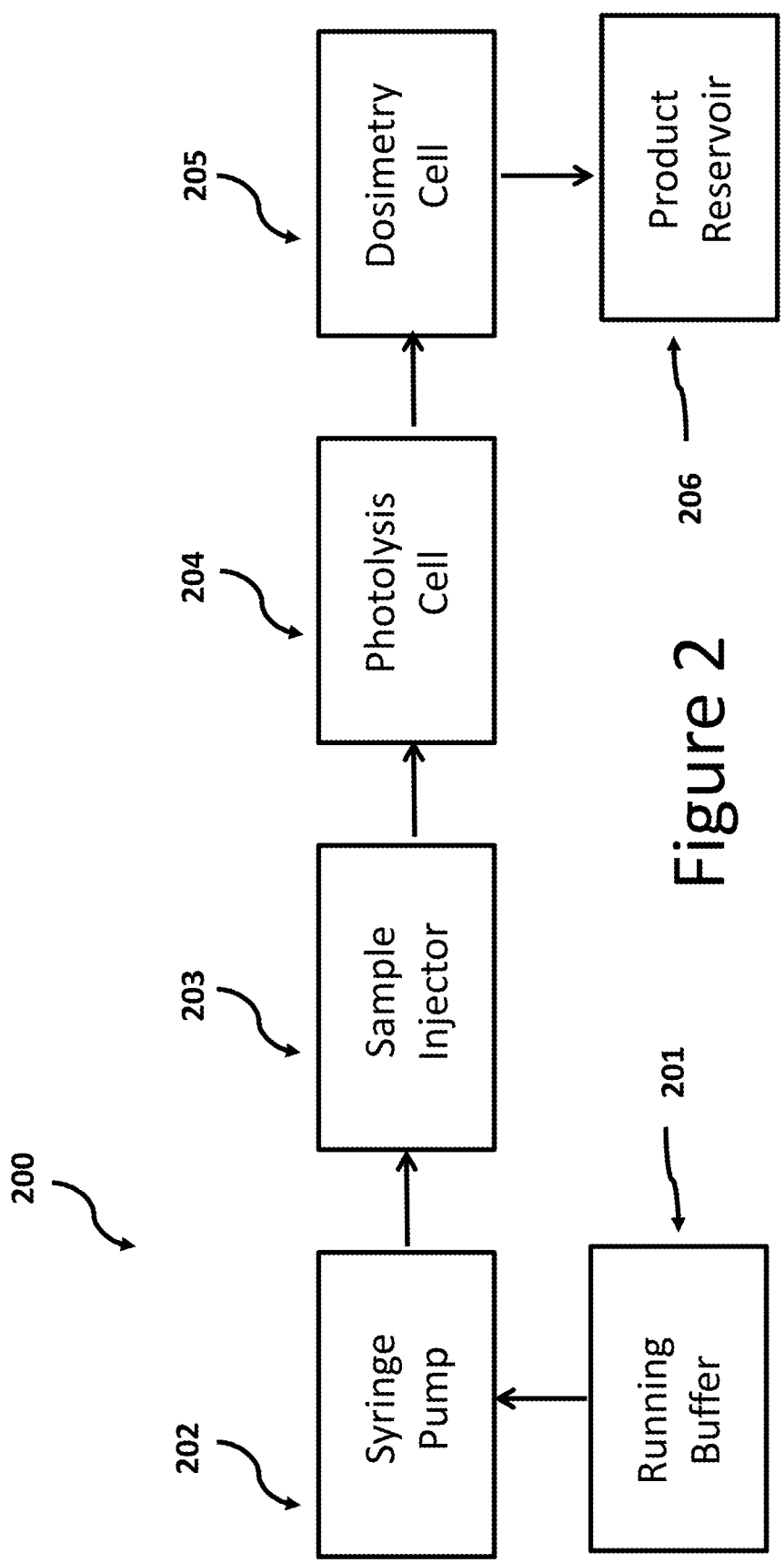
FIG. 2 illustrates movement of a sample through the flash photo oxidation apparatus 100 for analysis, according to various embodiments of the invention.

FIG. 2 illustrates movement of a sample through the flash photo oxidation apparatus 100 for analysis, according to various embodiments of the invention. Shown are: running buffer reservoir 201; syringe pump 202; sample injector 203; photolysis cell 204; dosimetry cell 205; and product reservoir 206. Arrows illustrate movement of sample/analyte between components. The elements illustrated in FIG. 2 are typically included in sample introduction system 101 of photolysis cell 102. Sample introduction system 101 is configured to provide a sample mixture including a molecular analyte and a buffer to photolysis cell 102.

Running buffer reservoir 201 contains fluid that serves to pump samples through the (micro)fluidic circuit is used to fill the bore of a syringe pump 202. In some embodiments, the running buffer fluid is high purity grade water. In some embodiments, the running buffer fluid is the buffer system employed to solubilize and stabilize the biological molecule. In some embodiments, the running buffer fluid includes the intrinsic radical dosimeter buffer(s) employed to solubilize and stabilize the biological molecule, while concomitantly providing an internal standard to perform radical dosimetry. Under microprocessor control, the syringe pump functions to pump running buffer and biological sample through the fluidic circuit. In some embodiments, the syringe pump is manually controlled by the user. The biological sample to be labeled is introduced into the flowing stream of running buffer by using an in-line sample injector 203. In some embodiments, the sample injector is a multi-port valve containing a sample injection loop as typically employed in liquid chromatography, and is manually operated by the user. In some embodiments, sample injector is operated by an electro-mechanical or pneumo-mechanical actuator under microprocessor control.

In some embodiments, the injected sample is mixed with hydrogen peroxide and an extrinsic internal standard radical dosimeter. In some embodiments, the injected sample is prepared using an intrinsic radical dosimeter buffer and is mixed with hydrogen peroxide. In some embodiments, the injected sample is prepared as noted above but does not contain hydrogen peroxide. After injection, the sample is pumped into the photolysis cell 204 where it may be irradiated by the photolysis light source. After flowing through the photolysis cell, the sample is pumped into the dosimetry cell 205, where the photometric properties of the sample solution are measured. Such photometric properties may include, but not be restricted to, ultra violet photometric absorbance. After leaving the dosimetry cell, the product is typically pumped into and collected by a product reservoir 206.

During initial operation of the system, a base-line measurement of the sample's photometric property is optionally taken. The baseline measurement is performed for the introduced sample without any photolysis. Once the baseline measurement is made, photolysis proceeds and once the photo-exposed sample, or labeled product, enters the dosimetry cell, the photometric property of the product is assessed. In some embodiments, product reservoir 206 contains more than one fluid storage compartments. In one compartment, unlabeled sample that flows through the system during the baseline measurement process is collected. In another compartment, labeled sample that flows through the system is collected. Product reservoir is optionally part of an automated product collection system for the purpose of collecting at least one product solution from the processing of said sample using OH radical reactions in the photolysis cell 102. In some embodiments, flash photo oxidation apparatus 100 further includes an instrument, such as an LC-MS, MS/MS or other instrument types disclosed herein, configured to detect which amino acids of a molecular analyte have been oxidized by reaction with OH radicals. This information may be used to determine a three-dimensional structure of the molecular analyte. The automated collection system may be configured for transferring the reacted sample mixture to this instrument.

Operational Cascade and Decision Matrix

FIG. 3 illustrates methods 300 of sample labeling and analysis, according to various embodiments of the invention. Shown are: a sample introduction step 301 in which a sample to be labeled is introduced; a measurement step 302 for photometric measurement of the non-irradiated sample; irradiation of the sample to initiate the labeling process 303; photometric measurement of the irradiated sample 304; assessment of the effective OH radical concentration by analyzing the change in the sample's photometric property after irradiation 305; the labeled sample is subsequently handled (e.g., analyzed using detector 116) after achieving desired effective OH radical concentration 306; decision tree element for how the labeled sample is subsequently handled after not achieving desired level of effective OH radical concentration 307; repeat cycle for adjusting flash spectral irradiance and/or $H_2O_2$ concentration 308.

In sample introduction step 301, a sample to be analyzed is introduced, e.g., via sample injector 203. The sample includes a mixture having at least a molecular analyte of interest and a buffer. The buffer is optionally selected to operate as an internal standard indicative of oxidation by OH radicals. The sample mixture may be prepared by selecting the buffer and adding the selected buffer to the molecular analyte as a precursor to step 301. The buffer is optionally selected to both control pH of the sample mixture and to also function as an internal standard representative of OH radical reactions with the molecular analyte.

The introduced sample mixture is first measured in its un-irradiated state to assess its nascent photometric property in measurement step 302. This initial measurement may be made using photolysis cell 102, photolysis system 103 and radical dosimeter 104 and serves as a baseline measurement against which subsequent photometric property measurements can be compared.

In an irradiate sample step 303, the introduced sample is irradiated in the photolysis cell 102, e.g., using a first light pulse from photolysis system 103. The irradiation of step 303 is configured to cause OH radical reactions with both the molecular analyte and the buffer.

In a measure step 304 a photometric measurement of the irradiated sample is then performed using radical dosimeter 104. In step 304 change in photometric property of the sample mixture is determined. The change includes a change in photometric property of the buffer and/or representing a measure of OH radical reactions with the molecular analyte. Results of measure step 304 can be compared with the results of measurement step 302 to assess for any change in photometric properties in analyze step 305. The change in photometric properties is used to determine an effective change in OH radical concentration within the sample. The photometric measurement is optionally also used to measure change in photometric property of the buffer to estimate an amount of OH radical scavenging within the sample mixture.

If a target OH radical concentration is achieved, the labeling process is continued and the product ultimately collected for further analysis in process step 306. Process step 306 optionally includes analysis using detector 116. This analysis may be configured to generate data indicating which parts (e.g., amino acids) of the molecular analyte have been oxidized by OH radical reactions. This information can be used to deduce which parts of the molecular analyte are on the surface of the molecular analyte, and there by deduce information about the three-dimensional structure of the molecular analyte. In a specific example detector 116 includes a mass spectrometer and process step 306 includes analyzing the product to identify amino acids reacted with OH radicals.

Should the target OH radical concentration not be achieved, then in an adjust step 307 the photolysis system fluence and/or $H_2O_2$ concentration is varied and the cycle repeated 308 to generate a new level of OH radical yield. Steps 303, 304 305, 307 and 308 may be performed 1, 2, 3 or more times as part of irradiation-measurement cycles before a desired OH radical concentration is achieved and the method proceeds to process step 306. The next cycle can include irradiating the sample mixture with at least a second light pulse from the pump light source in response to the change in photometric property of the buffer. The second light pulse is configured to cause additional OH radical reactions with both the molecular analyte and the buffer. Typically, the step of irradiating the mixture with at least the second light pulse (a repeat of step 303) is dependent on a determination that additional reaction between the OH radicals and the molecular analyte is desirable, this determination being based on the change in photometric property of the buffer.

During of irradiation-measurement cycles the sample mixture may be kept in the pyrolysis cell 102 or moved to other places within a microfluidics system including the pyrolysis cell 102. In various embodiments, the movement between regions of the microfluidics system may be of a travel distance less than 3, 5, 6, 10, 15 20 or 30 mm, or any range there between. These regions of the microfluidics system are configured to receive light from light sources of the flash photolysis system 103 and the radical dosimeter 104, respectively.

In some embodiments, process 300 is manually operated by the user. In some embodiments, process 300 is automated under microprocessor control, e.g., under the control of feed-back logic within instrument controller 106 and/or control electronics 105. The adjustment to the photolysis system made in adjust step 307 can include changes in pulse intensity, irradiance, fluence and/or number of pulse provided. In some embodiments, the "adjustment" includes merely a determination that more irradiation-measurement cycles are desired.

The process 300 is optionally further performed on a reference mixture. In these embodiments, the change in photometric property of the sample mixture resulting in at least the first light pulse from the pump light source can be normalized based on the abundance of the reaction product within the irradiated reference mixture.

Closed-Loop Control Radical Dosimetry System

A technical limitation of FPOP HRPF arises from the reaction of OH radicals with background or non-analyte components in the sample, such as buffer constituents and incipient solutes. Variability in the degree of background scavenging causes trial-to-trial irreproducibility, which has limited comparative studies (Niu, B. et al.; *Dosimetry determines the initial OH radical concentration in fast photochemical oxidation of proteins (FPOP)*; Journal of the American Society for Mass Spectrometry; 2015). While OH radicals are excellent probes of protein topography, they also react with many compounds found in analytical preparations. Competition between target protein and background scavengers for free OH radicals exists. As such, to insure reproducible results it is necessary to measure the effective concentration of available hydroxyl radical to oxidize the target protein and to accordingly adjust total hydroxyl radical production.

In photochemistry, effective radical concentration is measured using a radical dosimeter, such as radical dosimeter 104. Ideally, a dosimeter would have: a simple relationship between effective radical concentration and dosimeter response; a simple, rapid, and non-destructive measurement means; and be unreactive to most proteins. US 2014/0030751 A1 teaches the use of radical dosimetry for the assessment of background scavenging. A means to determine free OH radical concentration by measuring the absorbance change of adenine, a radical dosimeter, is described. Adenine competes with the protein sample, as well as with radical scavengers within the buffer, with an established reaction rate, allowing for normalization of radical production to compensate for differences in radical scavenging. Unlike other successful radical dosimeters that rely upon mass spectrometry measurements, adenine-based radical dosimetry gives accurate measurements using simple UV absorbance (Buxton, G. V., et al., *Critical review of rate constants for the reactions of hydrated elctrons, hydrogen atoms, and hydroxyl radicals in aqueous solution*; J. Phys. Chem. Ref. Data; 1988). The reaction products of adenine with hydroxyl radicals have been well-characterized both experimentally and in high-level theory (Xie, B. et al, *Hydroxyl Radical Dosimetry for High Flux Hydroxyl Radical Protein Footprinting Applications Using a Simple Optical Detection Method*. Anal Chem, 2015.; Naumov, S. et al, *The energetics of rearrangement and water elimination reactions in the radiolysis of the DNA bases in aqueous solution (eaq- and \*OH attack): DFT calculations*. Radiat Res, 2008).

Figure 4:
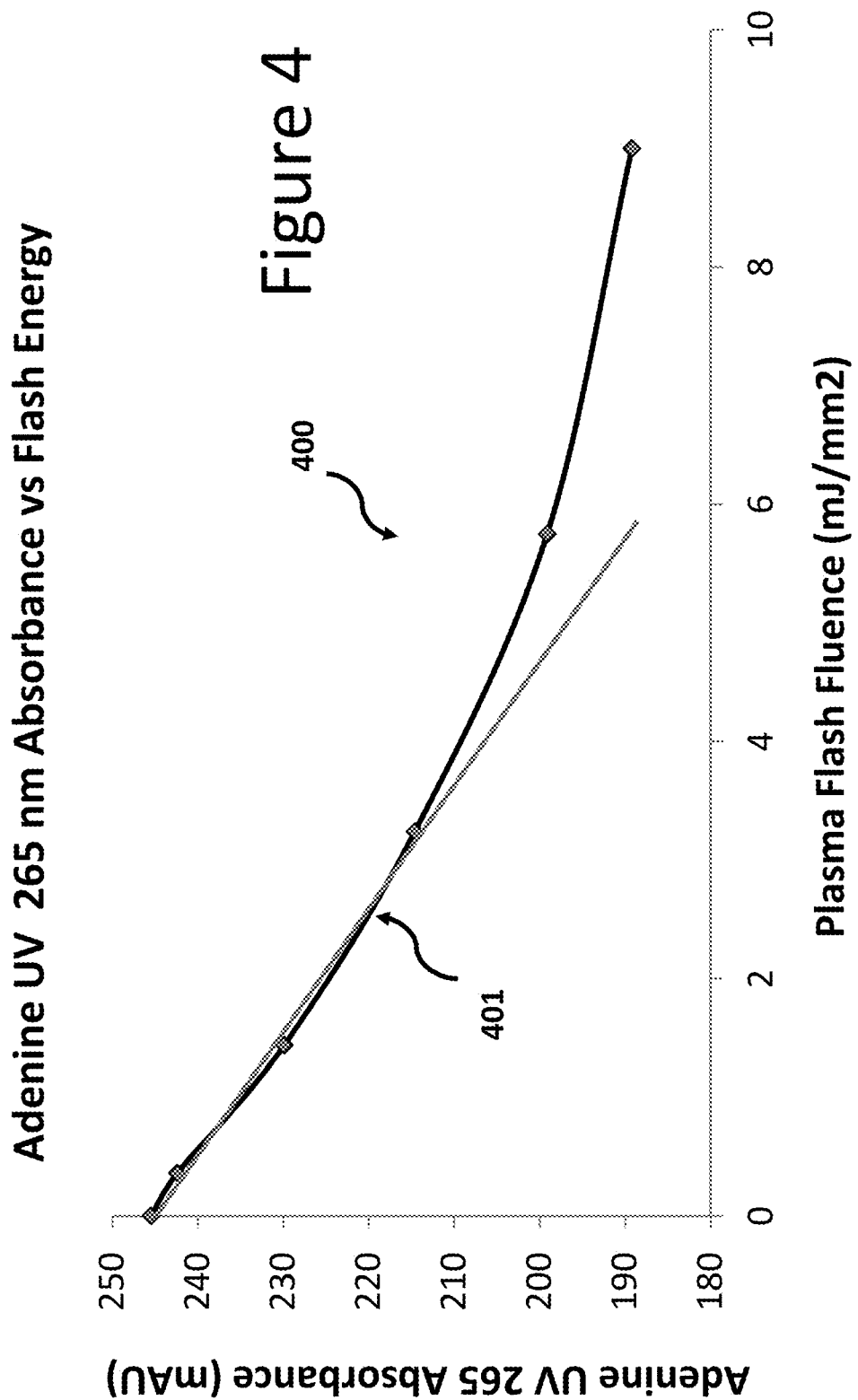
FIG. 4 is a depiction of the change in adenine UV 265 nm photometric absorbance 400 as a function of plasma flash fluence, according to various embodiments of the invention. Also shown is the linear dynamic range 401 for which the change in plasma flash fluence results in a proportional and linear change in adenine UV 265 nm absorbance.

As shown in FIG. 4, upon photo-oxidation, adenine loses UV absorbance at 265 nm. Briefly, a 1 mM adenine/100 mM $H_2O_2$ aqueous solution was measured for its ultraviolet (UV) photometric absorption of light at 265 nm when irradiated with a single flash of photolysis light from a plasma source (200-600 nm) at various fluence (0-9 $mJ/mm^2$). UV 265 absorbance of adenine reduces as plasma lamp fluence is increased. Within normal FPOP HRPF conditions for which the change in adenine absorbance is on the order of 5%-60%, the loss of UV adenine absorbance is linear 401 with effective hydroxyl radical concentration. Moreover, the loss of UV265 nm absorbance is not only linear by changes in applied fluence, but also by changes in generated OH radical or by variance of radical scavengers. The measured absorbance of adenine is also linear with protein and peptide oxidation products across a wide variety of amino acids, and adenine is unreactive under most conditions. As such, the variability in measured adenine absorbance change (before and after photo-exposure) can be assessed as a means to monitor changes in background scavenging. Once background scavenging has been assessed, corrections can be applied to compensate for trial to trial variability. In one means, photo-irradiance can be altered proportionally with changes in back-ground scavenging. Irradiance can be increased to compensate for increased levels of scavenging or decreased to address decreased levels of scavenging. In another means, the measured abundance of the oxidized species, as detected by mass spectrometry or some other detection scheme such as but not limited to isoelectric focusing electrophoresis, in two or more different trials could be normalized between runs by multiplying said response by a normalization factor derived from the ratio of adenine absorbance change for the different trials.

In US 2014/0030751 A1, an off-line means of collecting photo-exposed adenine and associated analyte protein is taught, where flow is diverted from a capillary photolysis cell and is directed to an off-line UV detector. The '751 approach consumes substantial product (several microliters) and requires much time to generate sufficient volume to transport the sample and to perform UV absorbance measurements. U.S. Provisional application 62/511,571 and International Application PCT/US18/34682 teach the means and methodology by which to perform radical dosimetry in real-time, as biologicals are labeled during the FPOP HRPF process. In this scheme, a photometric detection scheme is applied to the flowing stream of analyte in order to detect changes in the optical properties of an internal standard radical dosimeter. Optical property changes include but are not limited to: photometric absorbance, fluorescence; refractive index; and luminescence. Particular description is given to the use of adenine as an internal standard radical dosimeter that is added to the analytical sample as an exogenous or extrinsic component. Moreover, the '571 /'682 applications teach the means by which labeling parameters may be altered in real-time to achieve desired levels of effective OH radical concentration and associated labeling efficiency. Further, the '571 /'682 applications teach the means by which effective OH radical yield can be controlled by varying the fluence and/or spectral irradiance of a plasma flash lamp source in addition to dithering $H_2O_2$ concentration. Additionally, the '571 /'682 applications teach the means by which FPOP HRPF can be performed using photo-catalytic metal oxides that function to generate OH radicals from water, thus eliminating the reliance upon $H_2O_2$.

Intrinsic Radical Dosimetry

Prior art applications of photometric radical dosimetry made use of an extrinsic or "spike-in" additive, such as adenine, to the biological molecular solution under study. While this process is compatible with a majority of biochemical species and biopharmaceuticals, the presence of adenine or other extrinsic radical dosimeter internal standards could interact with the bio-species of interest and cause artifactual alteration of its nascent higher order structure. The latter is exemplified when studying a number of enzymes that make use of adenine containing high energy nucleotides to catalyze enzymatic reactions. In this case, it is desirable to use an internal standard radical dosimeter that does not interact with the target biomolecule and does not deleteriously impact nascent higher order structure.

Various embodiments rely on organic buffers that are routinely used for stabilizing and preserving biomolecular nascent structures to act as intrinsic radical dosimeter internal standards when used in FPOP HRPF studies. Generally, these intrinsic radical dosimeter standards have their photometric properties altered by OH radical attack. For UV photometric absorbance, there are two possible general classes of intrinsic dosimeters: type one intrinsic dosimeters which demonstrate reduced UV absorbance upon radical attack; and type two intrinsic dosimeters which demonstrate increased UV absorbance upon radical attack. For type one dosimeters the reduction in UV absorbance can result from OH radical attack and subsequent compromise of the buffer's UV absorbing chromophore. Conversely for type two dosimeters, OH radical attack can create chromophores from precursor aliphatic moieties. For photometric UV absorbance, type one intrinsic dosimeters include but are not limited to: HEPES (4-(2-hydroxyethyl)-1-piperazineethanesulfonic acid); MOPS (3-(N-morpholino) propanesulfonic acid); and PIPES (piperazine-N-N'-bis(2-ethanesulfonic acid). For UV photometric absorbance, type two intrinsic dosimeters include but are not limited to: Tris (Tris(hydroxymethyl)aminomethane) or (2-Amino-2hydroxymethyl)propane-1,3 diol); Tricine (3-[N-Tris(hydroxymethyl)methylamino]-2-hydroxypropanesulfonic acid); TES (2-[[1,3-dihydroxy-2-(hydroxymethyl)propane-2-yl]amino] ethanesulfonic acid); and TAPS (([tris(hydroxymethyl) methylamino]propanesulfonic acid). One of ordinary skill in the art will understand that other buffers may be used as intrinsic internal standards in addition to or as alternatives to the above examples.

Figure 5:
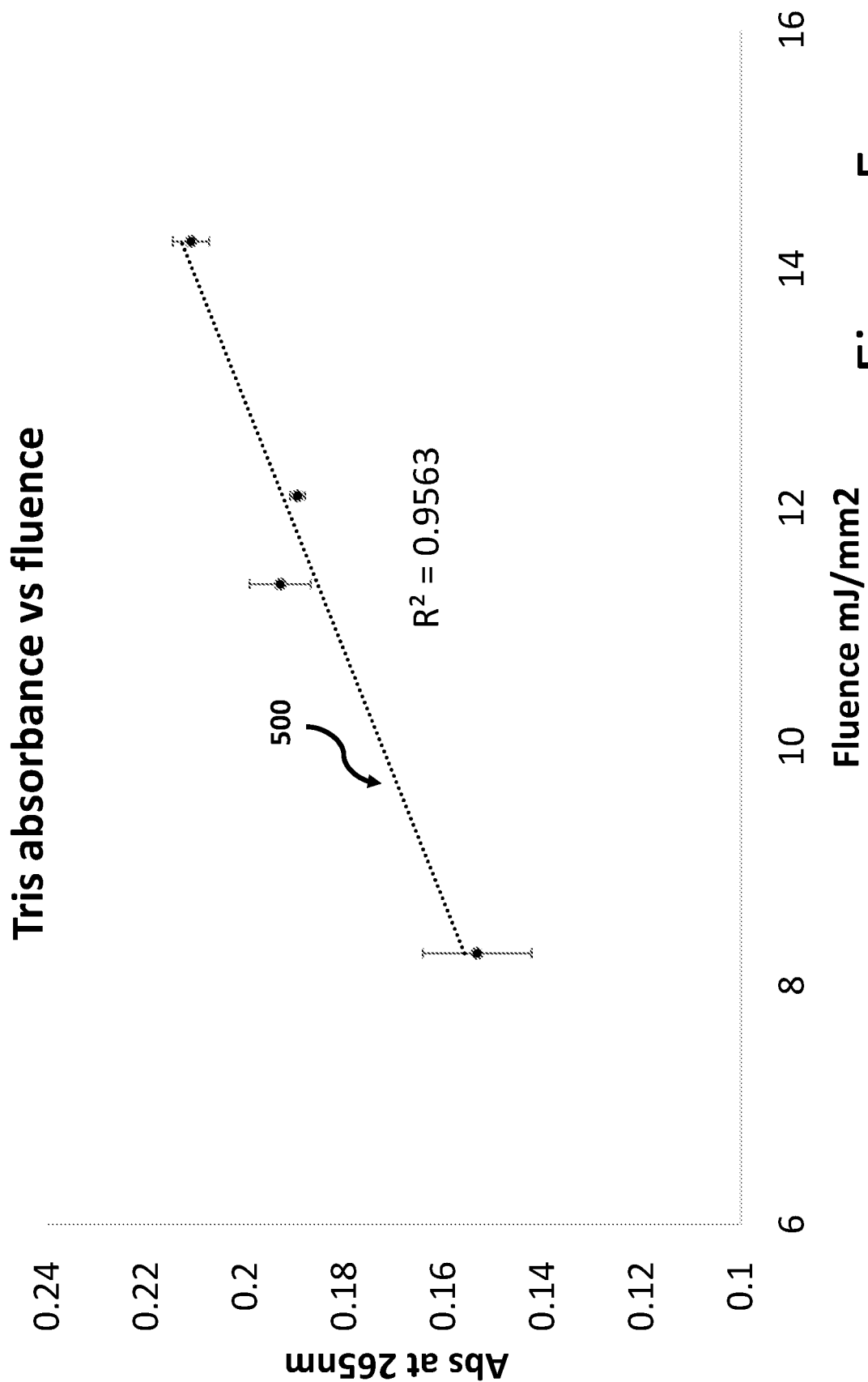
FIG. 5 illustrates is a plot 501 of the relationship between the UV 265 nm photometric absorbance of Tris buffer as a function of applied Excimer KrF laser fluence at 247 nm, according to various embodiments.

FIG. 5 illustrates is a plot 501 of the relationship between the UV 265 nm photometric absorbance of Tris buffer (a type II intrinsic dosimeter) as a function of applied Excimer KrF laser fluence at 247 nm, according to various embodiments. Briefly, a 100 mM solution of Tris was prepared containing a 100 mM of hydrogen peroxide. The UV 265 nm absorbance of the Tris solution was determined after a single shot exposure at the noted fluence values. As can be seen, the UV 265 nm absorbance of Tris increases with applied fluence in a highly linear and predictable manner Moreover, the nascent UV 265 nm absorbance of Tris was determined to be 0.0145 AU, which is more than 10 fold less than that for irradiated Tris. These results indicate that Tris is a viable candidate to act as an intrinsic radical dosimeter internal standard, in at least one embodiment of the invention.

Figure 6:
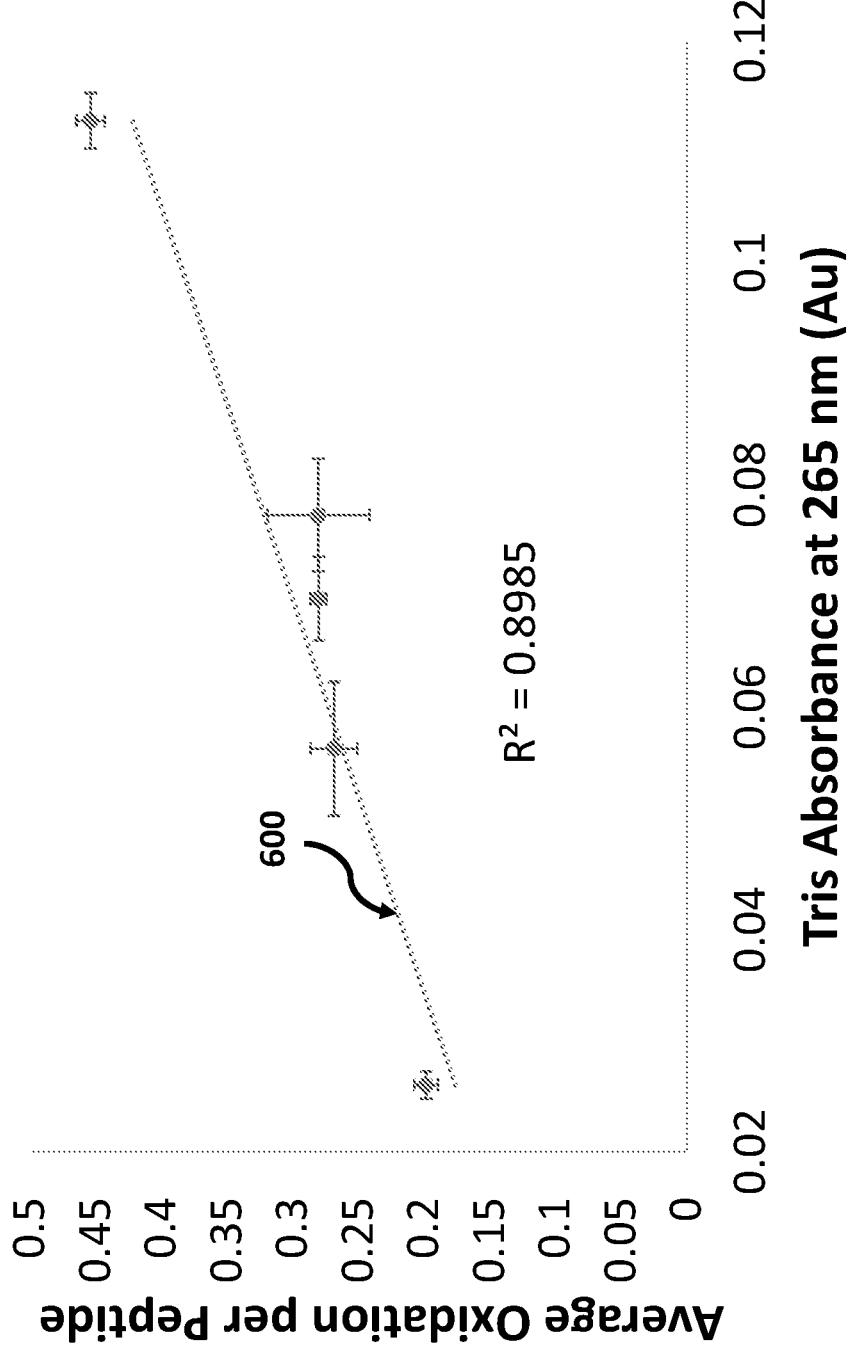
FIG. 6 illustrates the linear relationship 600 between the average number of oxidations per glu-1-fibrinopeptide b and Tris 265 nm UV absorbance when the peptide is treated with constant Excimer KrF laser fluence at 247 nm while mixed with 100 mM Tris and 100 mM $H_2O_2$, according to various embodiments.

In order to demonstrate the utility of Tris as an intrinsic radical dosimeter, FPOP HRPF labeling of a 1 uM solution of [Glu]-1-Fibrinopeptide b was performed using 100 mM Tris buffer employing varying concentrations of $H_2O_2$ (0-40 mM), applying a constant fluence (11 mJ/mm$^2$) from an Excimer KrF laser operated at 247 nm. The labeled peptide was subsequently analyzed by LC MS to assess the resultant oxidative content for its constituent amino acid residues. The average number of oxidations per peptide was determined for each $H_2O_2$ concentration and the results plotted against the measured Tris UV 265 nm absorbance for each photo-irradiated sample. As depicted in FIG. 6, there is linear relationship 600 between the average number of oxidized residues for Glu-1 and the UV 265 nm photometric absorption of Tris. As such, Tris UV absorbance is taken to be directly proportional to the effective OH radical load, demonstrating its utility as an intrinsic radical dosimeter internal standard.

Figure 7:
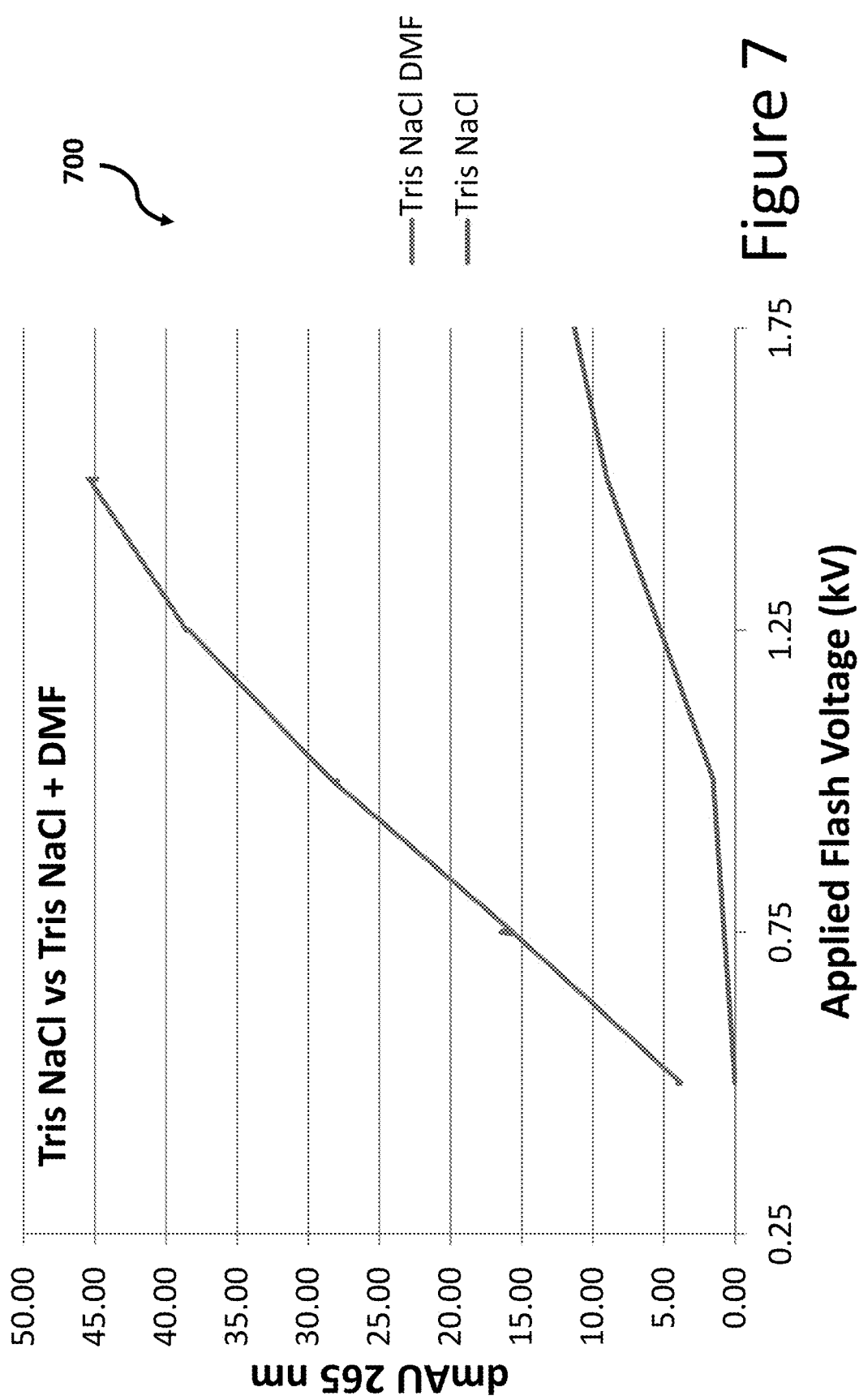
FIG. 7 illustrates the linear relationship 701 between the change in UV 265 nm photometric absorbance and applied flash voltage for the flash oxidation photolysis of $H_2O_2$ to create hydroxyl radicals that attacks solubilized 0.05% dimethyl foramide in 20 mM Tris, 150 mM NaCl buffer along with the UV photometric absorbance change for Tris/NaCl buffer alone, according to various embodiments.

Dimethyl foramide (DMF) in combination with Tris NaCl buffer has been shown to be an effective type 2 intrinsic radical dosimeter. As illustrated in FIG. 7, the UV photometric absorbance change at 265 nm for a 0.05% DMF 10 mMTris/150 mM NaCl buffer system is positively correlated with the applied flash voltage of a flash oxidation (FOX) FPOP system as described in US 2018/034682. When compared to Tris buffer alone, the DMF-Tris/NaCl system demonstrates a greater change in UV absorbance in response to applied flash voltage, making it a more sensitive type 2 intrinsic radical dosimeter.

The above noted buffer intrinsic radical dosimeter standards are intended to be exemplary of the invention and are not meant to be restrictive in scope. Clearly other specific buffer intrinsic dosimeter standards could be identified by those ordinarily skilled in the art, and such discoveries are deemed to be supplemental and not exclusive of the present invention.

Calibrating the Closed-Loop Control Radical Dosimetry System

In some embodiments, the closed-loop control radical dosimetry system comprises a calibration function that is used to predict the required change in optical fluence or hydrogen peroxide concentration in response to measured radical dosimeter photometric absorbance change. The calibration function is empirically determined through a plurality of measurements for which a known or control mixture of supporting buffer, analytical sample, and radical dosimeter are treated with a single flash of light for each distinct control aliquot at a various fluence or $H_2O_2$ concentration levels. In some embodiments, a software routine running in either the low level instrument control (e.g., control electronics 105) or high level user interface programs (e.g., Instrument controller 106), is configured to generate and/or use a look-up table that describes the measured change in dosimeter photometric absorbance at each fluence or $H_2O_2$ concentration, allowing for the creation of a mathematical expression, or calibration function, that describes the relationship between applied fluence and/or $H_2O_2$ concentration and measured dosimeter absorbance change for a single flash exposure. In some embodiments, the look-up table and subsequent calibration function is manually generated by the user employing absorbance change values for each pump source drive voltage value as reported by the present invention.

During sample processing, background hydroxyl radical scavenging is assessed via dosimetry. The measured change in dosimeter photometric absorbance is compared to a user specified targeted change. When the measured dosimeter value deviates by ≥+/−10% from the target value, the applied fluence or $H_2O_2$ concentration is altered to achieve the targeted change of measured dosimeter absorbance. The calibration function is used to predict the required change in fluence or $H_2O_2$ concentration. In some embodiments, these operations are included in adjust step 307.

Post-Analytical Normalization of Labeled Product Abundance

The systems and methods discussed herein alter spectral irradiance as a means to adjust for unwanted changes in background scavenging of OH radicals, and as such represent a pre-analytical or pre-data processing scheme of correction. In some embodiments, it is also possible to apply scavenging correction to acquired HRPF data in a post-analytical or data processing manner During post-analytical correction, the measured abundance of the oxidized species for an experimental trial, as detected by mass spectrometry or some other detection scheme such as but not limited to isoelectric focusing electrophoresis, is normalized by multiplying said response by a normalization factor derived from the ratio of dosimeter absorbance change determined between the experimental trial and reference trial. Normalization can be accomplished using standardization logic included in instrument controller 106 and/or control electronics 105. Specifically, in some embodiments, the normalization factor is the ratio of the measured dosimeter absorbance change of the experimental trial divided by the measured dosimeter absorbance change of the reference trial. Alternatively, the normalization factor can comprise the ratio of the measured dosimeter absorbance change of the reference trial divided by the experimental trial. In this manner, for example, the ion current for a given protein mass spectrometry (MS) measurement or peptide single MS or tandem MS measurement can be adjusted by multiplying said ion current value by the determined normalization factor. Such normalization schemes may be included in process step 306. For the purposes of disclosure, preanalytical and post-analytical normalization schemes have been individually discussed. It should be recognized that the application of these two schemes are not mutually exclusive, and can be employed in tandem to achieve higher levels of compensation than achievable by exclusive application. In some embodiments, post-analytical normalization is applied to data acquired from HRPF experiments performed under the control of pre-analytical scavenging correction. In some embodiments, standardization logic is configured to use the photometric properties of the buffer to quantitate background scavenging of OH radicals in the sample and/or to normalize an analysis between different experimental runs or trials.

Exemplary Sample Preparation and Analysis Protocols to Perform Flash HRPF

The following passages describe sample preparation and analysis protocols for the purpose of analyzing samples by flash HRPF according to some embodiments of the invention. While illustrative, these protocols are not meant to be limiting in scope, as variants exist and would be evident to those skilled in the art. Moreover, alterations in flash voltage could be substituted by appropriate change in $H_2O_2$ concentration. Further, the same protocol and control loop logic is applicable to laser based FPOP HRPF experiments.

Flash HRPF Using $H_2O_2$ and Internal Standard Radical Dosimeter

Analyte protein (~1-5 μM) is composed in solution with glutamine (17 mM), adenine (1 mM), and hydrogen peroxide (100 mM). Alternatively, the sample can be prepared using an intrinsic radical dosimeter buffer, thus obviating the use of adenine. Sample is introduced to the photolysis cell using flow rate of 10-100 microliters per minute. Flash photolysis and dosimetry is then performed. The UV absorbance of the dosimeter is fed-back into the flash lamp control system to deliver a consistent and reproducible effective concentration of hydroxyl radical to the solution as measured by a consistent loss of fractional absorbance at 260 nm (e.g. to maintain a 10% loss of absorbance), compensating for variances in flash lamp output, scavengers in solution, and changes in hydrogen peroxide concentration. Shortly after processing, the sample is deposited into a quenching solution consisting of a final concentration of 70 mM methionine amide and 1 μM catalase. The oxidized sample is later proteolytically digested and used for LC-MS(/MS) (liquid chromatography and mass spectrometry) analysis of peptide and amino acid oxidation Amino acids disposed at a surface of a molecular analyte are more likely to undergo reactions with OH radicals relative to amino acids disposed at an interior of the molecular analyte. As such, the oxidation or lack thereof of the amino acids is indicative of which amino acids are exposed at the surface and of the three-dimensional structure of the analyte molecule. Further, changes in protein topography can be determined based on changes in the amount of oxidation of affected amino acids compared to a reference protein footprint.

It should be apparent, however, to those skilled in the art that many more modifications besides those already described are possible without departing from the inventive concepts herein. The inventive subject matter, therefore, is not to be restricted except in the spirit of disclosure.

All patent publications, patents, and patent applications cited herein or filed with this application are incorporated by reference in their entirety.

The general structure and techniques, and more specific embodiments which can be used to effect different ways of carrying out the more general goals are described herein. Although only a few embodiments have been disclosed in detail above, other embodiments are possible and the inventor(s) intend these to be encompassed within this specification. The specification describes specific examples to accomplish a more general goal that may be accomplished in another way. This disclosure is intended to be exemplary, and the claims are intended to cover any modification or alternative that might be predictable to a person having ordinary skill in the art.

The computing devices described herein may be of any kind of computer, either general purpose, or some specific purpose computer such as a workstation or laboratory or manufacturing equipment. "Programs" or "logic" discussed herein include hardware, firmware, and/or computing instructions stored on a non-transient medium. For example feed-back logic can include a processor and other circuits configured for determining if additional OH radical reactions are desirable for an irradiated sample.

COPYRIGHT NOTICE

Pursuant to 37 C.F.R. 1.71(e), applicant notes that a portion of this disclosure contains material that is subject to and for which is claimed copyright protection (such as, but not limited to, source code listings, screen shots, user interfaces, or user instructions, or any other aspects of this submission for which copyright protection is or may be available in any jurisdiction.). The copyright owner has no objection to the facsimile reproduction by anyone of the patent document or patent disclosure, as it appears in the Patent and Trademark Office patent file or records. All other rights are reserved, and all other reproduction, distribution, creation of derivative works based on the contents, public display, and public performance of the application or any part thereof are prohibited by applicable copyright law.

What is claimed is:

1. An analysis system comprising:
   a flash photolysis system for irradiating a sample containing a photo-reactive sample mixture, the sample mixture including at least a molecular analyte and a buffer, the flash photolysis system being configured to cause OH radical reactions with both the analyte and the buffer;
   a photolysis cell, of the flash photolysis system, in optical communication with a flash photolysis system light source and configured to receive the sample containing the photo-reactive sample mixture;
   a radical dosimeter configured to receive fluid from the photolysis cell and configured for detecting photometric properties of the buffer; and
   feed-back logic configured to further irradiate the sample using the flash photolysis system responsive to the detected photometric properties of the buffer, the buffer selected to function as an internal standard indicative of a quantitation of OH radical reactions with the molecular analyte.

2. The system of claim 1, wherein the photometric property of the buffer measured by the radical dosimeter is UV photometric absorption.

3. The system of claim 1, wherein the photometric property of the buffer measured by the radical dosimeter is fluorescence.

4. The system of claim 1, wherein the photometric property of the buffer measured by the radical dosimeter is luminescence.

5. The system of claim 1, wherein the photolysis cell is disposed within a microfluidics system.

6. The system of claim 1, further comprising standardization logic configured to use the photometric properties of the buffer to quantitate background scavenging of OH radicals in the sample.

7. The system of claim 1, wherein the feed-back logic is configured to irradiate the sample using the flash photolysis system and measure the photometric properties of the buffer within the photolysis cell, for several irradiation-measurement cycles during which the sample remains in the photolysis cell.

8. The system of claim 7, wherein the feed-back logic is configured to repeat the irradiation-measurement cycles until a desired amount of reaction between the buffer and OH radicals has been achieved.

9. The system of claim 1, wherein the buffer includes
   at least one of Tris (Tris(hydroxymethyl)aminomethane) or (2-Amino-2hydroxymethyl)propane-1,3 diol);
   Tricine (3-[N-Tris(hydroxymethyl)methylamino]-2-hydroxypropanesulfonic acid); TES (2-[[1,3-dihydroxy-2-(hydroxymethyl)propane -2-yl]amino]ethanesulfonic acid); and
   TAPS (([tris(hydroxymethyl)methylamino]propanesulfonic acid).

10. The system of claim 1, wherein the radical dosimeter is configured for detecting the photometric properties of the buffer within the photolysis cell.

11. The system of claim 1, wherein the radical dosimeter is configured for detecting the photometric properties of the buffer within a microfluidics system that includes the photolysis cell.

12. The system of claim 1, wherein the radical dosimeter is configured for detecting the photometric properties of the buffer at a location within a microfluidics system that includes the photolysis cell, the location being between 3-30 mm from the photolysis cell, the microfluidics system being configured for moving the sample mixture back and forth between the photolysis cell and the location at which the photometric properties of the buffer are detected.

13. A method of determining a three-dimensional structure of a molecular analyte, the method comprising:
   adding a buffer to a molecular analyte to form a sample mixture, the buffer being selected to both control pH of the sample mixture and to function as an internal standard representative of OH radical reactions with the molecular analyte;
   introducing the sample mixture into a photolysis cell of a flash photolysis system, the sample mixture including at least a molecular analyte and a buffer;
   determining a photometric property of the sample mixture;
   irradiating the sample mixture with at least a first light pulse from a pump light source, the first light pulse being configured to cause OH radical reactions with both the molecular analyte and the buffer;
   determining a change in photometric property of the sample mixture, the change including a change in photometric property of the buffer and representing a measure of OH radical reactions with the molecular analyte;
   irradiating the sample mixture with at least a second light pulse from the pump light source in response to the change in photometric property of the buffer, the second light pulse being configured to cause additional OH radical reactions with both the molecular analyte and the buffer; and
   analyzing a product produced from the irradiated sample mixture after being irradiated with both the first and second light pulses to generate data regarding a three-dimensional structure of the molecular analyte.

14. The method of claim 13, further comprising adjusting a spectral irradiance of the pump light source in response to the change in photometric property of the buffer, prior to irradiating the mixture with at least the second light pulse.

15. The method of claim 13, wherein the photometric property of the buffer is a photometric absorption property.

16. The method of claim 13, wherein the photometric property of the buffer is a fluorescence property.

17. The method of claim 13, wherein the photometric property of the buffer is a luminescence property.

18. The method of claim 13, further comprising using the change in photometric property of the buffer to measure an amount of OH radical scavenging within the sample mixture.

19. A method of determining a three-dimensional structure of a molecular analyte, the method comprising:
   introducing a sample mixture into a photolysis cell of a flash photolysis system, the sample mixture including at least a molecular analyte and a buffer;
   determining a photometric property of the sample mixture;
   irradiating the sample mixture with at least a first light pulse from a pump light source, the first light pulse being configured to cause OH radical reactions with both the molecular analyte and the buffer;

determining a change in photometric property of the sample mixture, the change including a change in photometric property of the buffer and representing a measure of OH radical reactions with the molecular analyte;

irradiating the sample mixture with at least a second light pulse from the pump light source in response to the change in photometric property of the buffer, the second light pulse being configured to cause additional OH radical reactions with both the molecular analyte and the buffer, the step of irradiating the mixture with at least the second light pulse being is dependent on a determination that additional reaction between the OH radicals and the molecular analyte is desirable, this determination being based on the change in photometric property of the buffer; and analyzing a product produced from the irradiated sample mixture after being irradiated with both the first and second light pulses to generate data regarding a three-dimensional structure of the molecular analyte.

20. The method of claim 19, further comprising adjusting a spectral irradiance of the pump light source in response to the change in photometric property of the buffer, prior to irradiating the mixture with at least the second light pulse.

21. The method of claim 19, wherein the photometric property of the buffer is a photometric absorption property.

22. The method of claim 19, wherein the photometric property of the buffer is a fluorescence property.

23. The method of claim 19, wherein the photometric property of the buffer is a luminescence property.

24. The method of claim 19, further comprising using the change in photometric property of the buffer to measure an amount of OH radical scavenging within the sample mixture.

* * * * *

UNITED STATES PATENT AND TRADEMARK OFFICE
CERTIFICATE OF CORRECTION

| | | |
|---|---|---|
| PATENT NO. | : 11,181,529 B2 | Page 1 of 1 |
| APPLICATION NO. | : 17/193913 | |
| DATED | : November 23, 2021 | |
| INVENTOR(S) | : Scot Randy Weinberger, Joshua S. Sharp and Sandeep Misra | |

It is certified that error appears in the above-identified patent and that said Letters Patent is hereby corrected as shown below:

In the Specification

Column 1, Line 28:
Please delete "grants R01GM127267 and R43GM125420" and insert --grant number R43 GM125420-- therefore.

Signed and Sealed this
Fourth Day of March, 2025

Coke Morgan Stewart
*Acting Director of the United States Patent and Trademark Office*